United States Patent
Morikawa et al.

[11] Patent Number: 5,953,445
[45] Date of Patent: Sep. 14, 1999

[54] LIGHT GUIDING MEMBER, LIGHT DETECTING DEVICE AND DEFECT INSPECTING APPARATUS

[75] Inventors: Masahiro Morikawa; Kazumi Furuta, both of Hino, Japan

[73] Assignee: Konica Corporation, Tokyo, Japan

[21] Appl. No.: 09/017,065

[22] Filed: Feb. 2, 1998

[30] Foreign Application Priority Data

Feb. 10, 1997 [JP] Japan .................................. 9-026377

[51] Int. Cl.$^6$ ...................................................... G06K 9/00
[52] U.S. Cl. ........................................... 382/141; 362/551
[58] Field of Search ..................................... 382/141, 149, 382/112; 362/551, 558; 356/339.1, 339.7, 339.8, 430, 443, 444, 431; 250/227.11, 559.02, 559.45, 559.48

[56] References Cited

U.S. PATENT DOCUMENTS

| | | | |
|---|---|---|---|
| 4,116,566 | 9/1978 | Sick | 356/431 |
| 5,243,402 | 9/1993 | Weber et al. | 356/429 |
| 5,448,350 | 9/1995 | Kohno | 356/237.2 |

*Primary Examiner*—Joseph Mancuso
*Assistant Examiner*—Vikkram Bali
*Attorney, Agent, or Firm*—Frishauf, Holtz, Goodman, Langer & Chick, P.C.

[57] ABSTRACT

A defect inspecting apparatus for optically inspecting a defect of a subject to be inspected, includes: a first light guiding member having a first columnar light transmitting member including a first side surface and a second side surface facing the first side surface, curvature of the first side surface being smaller than that of the second side surface, and a first light scattering band having a definite width provided on the second side surface of the first columnar light transmitting member in a columnar axis direction. The first light guiding member enables a transmitted light or a reflected light of a light illuminated to the subject to be inspected from a light source to enter the first side surface, a part of the light incident on the first side surface to guide substantially to the columnar axis direction of the first light guiding member thereby to reach an end thereof, the other part of the light incident on the first side surface to emit from the second side surface. The defect inspecting apparatus further includes: a first light detecting means for detecting the light guided to the circular end of the first light guiding member; and a light detecting device for detecting the light emitted from the second side surface of the first light guiding member.

14 Claims, 9 Drawing Sheets

LIGHT GUIDING MEMBER, LIGHT DETECTING DEVICE AND DEFECT INSPECTING APPARATUS

BACKGROUND OF THE INVENTION

The present invention relates to a light guiding member, light detecting device and defect inspecting apparatus. More specifically, the present invention relates to a light guiding member which can obtain both functions of a spectral function to separate the light into specular reflection light and diffuse reflection light, or into regular transmission light and diffuse transmission light, and of a light guiding function, by a single member, and to a light detection device using the light guiding member, and a defect inspecting apparatus.

Conventionally, in an optical system of a flying spot system, when a quantity of light at each scanning position is detected, the followings are well known: a light guiding member in which a diffuse reflection band is formed in a direction of a cylindrical axis of a cylindrical light transmission member for light transmission, as described in Japanese Patent Publication No. 39753/1979, Japanese Utility Model Publication No. 43762/1994, etc., and the light entering along the direction of the cylindrical axis is guided to a light detector provided at one end or both ends of the cylindrical light transmission member; and a light detecting device using the light guiding member.

Further, in the optical system of the flying spot system, when the surface inspection of a subject to be inspected is conducted by using the reflected light in which the light scans on the subject to be inspected (irradiated subject) and the light is reflected on the subject to be inspected, or by using the transmitted light in which the light transmits the subject to be inspected, it is well known that information necessary for defect inspection can be obtained more accurately and minutely, by separating the regular transmission light (or specular reflection light) from the diffuse transmission light (or diffuse reflection light), and by detecting a change of each quantity of light.

For example, as described in Japanese Patent Publication Open to Public inspection No. 220636/1984, an example is well known in which the defect inspection is conducted by using a slit mirror. A general view in the case where the defect is detected by using the slit mirror system, is shown in FIG. 1. In this connection, FIG. 1 shows a case in which the transmission light is detected, however, the reflection light can also be used.

An inspection light 1 irradiated from a light source transmits a transparent sheet-like subject to be inspected 2, and becomes 2 types of transmission light of a regular transmission light 4 and a diffuse transmission light 3. The regular transmission light 4 and the diffuse transmission light 3 enter a light receiving portion casing 100; by a slit mirror 5 in the light receiving portion casing 100, the regular transmission light 4 transmits a slit of the slit mirror 5, and a portion of the diffuse transmission light 3 is reflected by a mirror of the slit mirror 5; and thereby, the regular transmission light 4 and the diffuse transmission light 3 are separated from each other into the different directions. Then, the regular transmission light is detected by a regular transmission light detector 11, and a portion of the diffuse transmission light 3 is detected by a diffuse transmission light detector 8. Then, the defect inspection is conducted according to a change of quantity of light respectively detected by the regular transmission light detector 11 and the diffuse transmission light detector 8. In this connection, light detectors have light diffusing plates 6 and 9, and a plurality of photomultiplier tubes (PMT) (not shown). The light, which arrived at respective light detectors, is diffused by the light diffusing plates 6 and 9, made uniform, and then detected by a plurality of PMTs.

Further, another example is also well known in which a diffuse reflection band is formed in the direction of cylindrical axis of a cylindrical light transmission member for light transmission, 3 light guiding members are used in which the light entering along the direction of the cylindrical axis is guided to the light detector provided at one end or both ends of the light transmission member, and thereby, the regular transmission light (or specular reflection light) and the diffuse transmission light(or diffuse reflection light) are separated from each other, and changes of quantities of both light are detected.

In this case, 2 light guiding member are used for light receiving and light guiding of the diffuse transmission light (or diffuse reflection light), and one light guiding member is used for light receiving and light guiding of the regular transmission light (or specular reflection light). Further, a cylindrical lens is provided for converging the diffuse light in the front of the light guiding member for the diffuse transmission light (or diffuse reflection light).

A general view in the case of detection using 3 light guiding members is shown in FIG. 2. FIG. 2 shows the case of detection for reflection light, however, it can also be applied for the detection of the transmission light.

Three light guiding members, that is, the light guiding member 16 for the specular reflection light, and the light guiding members 19A and 19B for the diffuse reflection light are respectively located as shown in FIG. 2.

Detection light 13 is reflected by a sheet-like subject to be inspected 12, and is made to be 2 types of reflection light of specular reflection light 21, and diffuse reflection light 22 and 23. The specular reflection light 21 is received by the light guiding member for the specular reflection light 16. The diffuse reflection light 23 are converged by condenser lenses 20A and 20B for the diffuse reflection light, which are cylindrical lenses, and then, are received by light guiding members 19A and 19b for the diffuse reflection light.

The light guiding member 16 for the specular reflection light and the light guiding members 19A and 19B for the diffuse reflection light are manufactured by forming light scattering bands 15, 17A and 17B, by coating titan oxide particles on the light guiding members 14, 18A and 18B for light transmission.

The light respectively received by the light guiding member 16 for the specular reflection light, and light guiding members 19A and 19B for the diffuse reflection light, is scattered by the light scattering bands 15, 17A and 17B, transmitted through light transmission members 14, 18A and 18B in the direction of the cylindrical axis, guided to light detection means (not shown) located at respective end surfaces of the light guiding member 16 for the specular reflection light, and light guiding members 19A and 19B for the diffuse reflection light, and the defect inspection is conducted according to respective changes of quantities of light detected by the light detecting device by respective light.

However, when the regular transmission light (or specular reflection light) and the diffuse transmission light (or diffuse reflection light) are separated from each other, and the change of quantity of light of both light is detected by using the slit mirror system, there are following problems.

When the slit mirror system is used, because the light is separated into 2 directions of the regular transmission light (or specular reflection light) and the diffuse transmission light (or diffuse reflection light), the size of the casing of light receiving portion becomes large, resulting in the necessity of the large mounting space. Further, a large number of light detection means such as PMT are necessary, resulting in an increase of cost.

Further, in the slit mirror system, a loss of the diffuse transmission light (or diffuse reflection light) is large, (the light which can not enter the casing of light receiving portion, the light which passes the outside of the light diffusing plate 6 after having been reflected by the slit mirror 5, etc.), and only a portion of the diffuse transmission light (or diffuse reflection light) is received and used for the light detection. Accordingly, when the subject to be inspected is photosensitive material such as photographic light sensitive material, a quantity of the light used for the inspection is very small in order to prevent fogging, and as a result, it is necessary to detect a change of the quantity of light of a portion of a very small quantity of the diffuse transmission light (or diffuse reflection light), resulting in much difficulty and inaccuracy.

On the other hand, when 3 cylindrical light guiding members are used, and the regular transmission light (or specular reflection light) and the diffuse transmission light (or diffuse reflection light) are separated from each other, and the change of the quantities of both light are detected, the following problems occur.

At first, 3 light guiding members are used, resulting in a larger light detecting device and a larger mounting space.

Next, the divergence of diffused light becomes larger as the distance from the subject to be inspected becomes larger. Accordingly, in order to receive the diffused light as much as possible by the cylindrical light guiding member, the mounting position of the light guiding member for the diffuse transmission light (or diffuse reflection light)is limited, and therefore, the mounting position of the light detecting device is limited.

Further, when the light scans on the subject to be inspected such as the film-like material or the like, and the reflection light which is reflected by the subject to be inspected, or the transmission light which passes through the subject to be inspected, are used for inspecting the defect on the surface of the subject to be inspected, the diffusiveness of the diffused light is small in many cases. In particular, when the defect of the transparent film-like material or the like is inspected in such a manner that the transmission light obtained when the light scanning on the film passes through the film, is used for inspecting the defect on the surface of the subject to be inspected, the diffusiveness of the diffuse transmission light is small in many cases.

Further, the inventor of the present invention found that the diffused light (near the diverging angle of 2°–5°) near the regular transmission light (or specular reflection light) includes useful information for the defect inspection in many cases.

However, when 3 cylindrical light guiding members are used as shown in FIG. 2, it is physically rather difficult because of small diffusiveness that 3 cylindrical light guiding members are positioned so that the diffused light having small divergence of light and the diffused light near the regular transmission light (or specular reflection light), (for example, numeral 22 in FIG. 2, or the diffused light nearer the regular transmission light (not shown )),can be detected. Accordingly, in order to obtain the diffused light having small divergence of light and the diffused light near the regular transmission light (or specular reflection light), it is necessary to severely set the mounting positions of 3 cylindrical light guiding members.

SUMMARY OF THE INVENTION

The present invention was accomplished in view of the foregoing background. That is, an object of the present invention is to provide a light detecting device and a light guiding member useful for a defect inspecting apparatus, by which the defect of the irradiated object is inspected, in particular, by irradiating the inspection light onto the irradiated subject, and by detecting the regular transmission light (or specular reflection light) and the diffuse transmission light (or diffuse reflection light).

Another object of the present invention is to effectively detect changes of quantities of respective light by separating the regular transmission light (or specular reflection light) from the irradiated subject and the diffuse transmission light (or diffuse reflection light) from the irradiated subject from each other, and thereby to reduce the size and cost of the apparatus.

Further object of the present invention is to reduce a loss of the diffuse transmission light (or diffuse reflection light) by enabling receive and detection of the more diffuse transmission light (or diffuse reflection light). Thereby, still further object of the present invention is to enable the apparatus to perform accurate defect inspection of the photographic light sensitive material by the light detection, even when the quantity of light is very small at the time of defect inspection of the photographic light sensitive material.

Further object of the present invention is to enable the apparatus to obtain the diffuse transmission light (or diffuse reflection light) having small diffusiveness, and the diffuse transmission light (or diffuse reflection light) near the regular transmission light (or specular reflection light)without severely positioning the light receiving portion such as the light guiding member, or the like, and thereby to enable it to perform more accurate light detection and defect inspection.

The object of the present invention can be attained by any one of structures described below.

A defect inspecting apparatus to optically inspect the defect of a subject to be inspected, comprising:

(a) the first light guiding member comprising;

the first columnar light transmission member having the first side surface and the second side surface opposite to the first side surface, in which curvature of the first side surface is smaller than that of the second side surface; and the first light scattering band provided in the direction of the columnar axis with a predetermined width, on the second side surface of the first columnar light transmission member, wherein the first light guiding member causes the transmission light or reflection light of the light, emitted from a light source onto the subject to be inspected, to enter the first side surface, a portion of the light entered the first side surface is guided in the direction of almost columnar axis of the first light guiding member, and arrives at the circular end surface of the first light guiding member, and further, another portion of the light entered the first side surface is emitted from the second side surface;

(b) the first light detecting means to detect the light guided to the circular end surface of the first light guiding member; and (c) a light detecting device to detect the light emitted from the second side surface of the first light guiding member.

According to the present invention, the specular reflection light (regular transmission light) and the diffuse reflection light (diffuse transmission light) are separated from each other, thereby the size of the light detecting device to detect changes of quantities of respective light can be reduced and the device can be obtained at low cost.

Further, the diffuse transmission light (or diffuse reflection light) is converged by the first light guiding member, and the number of members through which the diffuse transmission light (or diffuse reflection light)passes is small. Accordingly, a loss of the diffuse transmission light (or diffuse reflection light) can be reduced, and thereby the more diffuse transmission light (or diffuse reflection light) can be detected. Thereby, the accurate defect inspection of the photographic light sensitive material by the light detection can be performed, even when the very small quantity of light is used for the defect inspection, such as the defect inspection of the photographic light sensitive material.

Further, the light guiding member for the specular reflection light (regular transmission light) and the light receiving member to receive the diffuse reflection light (diffuse transmission light) can be located on the same optical axis. The diffuse transmission light (or diffuse reflection light) having small diffusiveness, and the diffuse transmission light (or diffuse reflection light) near the regular transmission light (or specular reflection light) can be obtained without severely positioning the light guiding member, and thereby the more accurate light detection and defect inspection can be performed.

Further, the light is entered into the first side surface having a small curvature, thereby, a quantity of incident light reflected by the first side surface can be reduced. Thereby, a loss of both of the specular reflection light (regular transmission light) and the diffuse reflection light (diffuse transmission light) can be reduced. Further, the diffuse transmission light (or diffuse reflection light) having small diffusiveness, and the diffuse transmission light (or diffuse reflection light) near the regular transmission light (or specular reflection light) can be obtained without severely positioning the light guiding member, and thereby the more accurate light detection and defect inspection can be performed.

Further, the size of the apparatus can also be reduced.

Further, in the above-described defect inspecting apparatus, the first light guiding member guides the light whose diverging angle is within a predetermined angle in the incident light, in the direction of almost columnar axis of the light guiding member, and emits the light whose diverging angle is not smaller than a predetermined angle in the incident light, from the second side surface, wherein the predetermined angle is not larger than 5°.

Further, thereby, the diffuse reflection light (diffuse transmission light) near the specular reflection light (regular transmission light) and the specular reflection light (regular transmission light) can be separated from each other, and the diffuse reflection light (diffuse transmission light) near the specular reflection light (regular transmission light) which has useful information for the defect inspection in many cases, can be used for the defect inspection.

Further, even when the diffusiveness of the diffuse transmission light (or diffuse reflection light) is small, the defect inspection can be performed.

Further, the light guiding member for the specular reflection light(regular transmission light) and light receiving member which receives the diffuse reflection light (diffuse transmission light) can be located on the same optical axis. Thereby, without severely positioning the light guiding member for the specular reflection light(regular transmission light) and that for the diffuse reflection light (diffuse transmission light), etc., the light detecting device to detect the change of quantity of light of both light can be obtained.

(Meaning of terms)

In the present invention, "side surface" means the surface parallel to the columnar axis of the columnar light transmission member.

In the present invention, "the columnar light transmission member" means a columnar member to transmit the light.

In the present invention, "the light within the diverging angle of 5°" means the following. When, in the surface of the light guiding member-side of the irradiated object, the transmission point through which the light transmits, or the reflection point from which the light is reflected is defined as a center, and the specular reflection light or the regular transmission light is defined as an axis, it means the light within the range of not larger than 5° from the axis, that is, the light within the range of not larger than total 10°. In FIG. 8, "within the diverging angle of 5°" is shown as the range 300.

DETAILED DESCRIPTION OF THE PREFERRED EMBODIMENT

Examples of embodiments according to the present invention are shown below, however, the present invention is not limited to those examples. Further, the embodiments described below show preferred examples of the present invention, and do not limit the meaning of terms and the scope of technology of the present invention.

Figure 1:
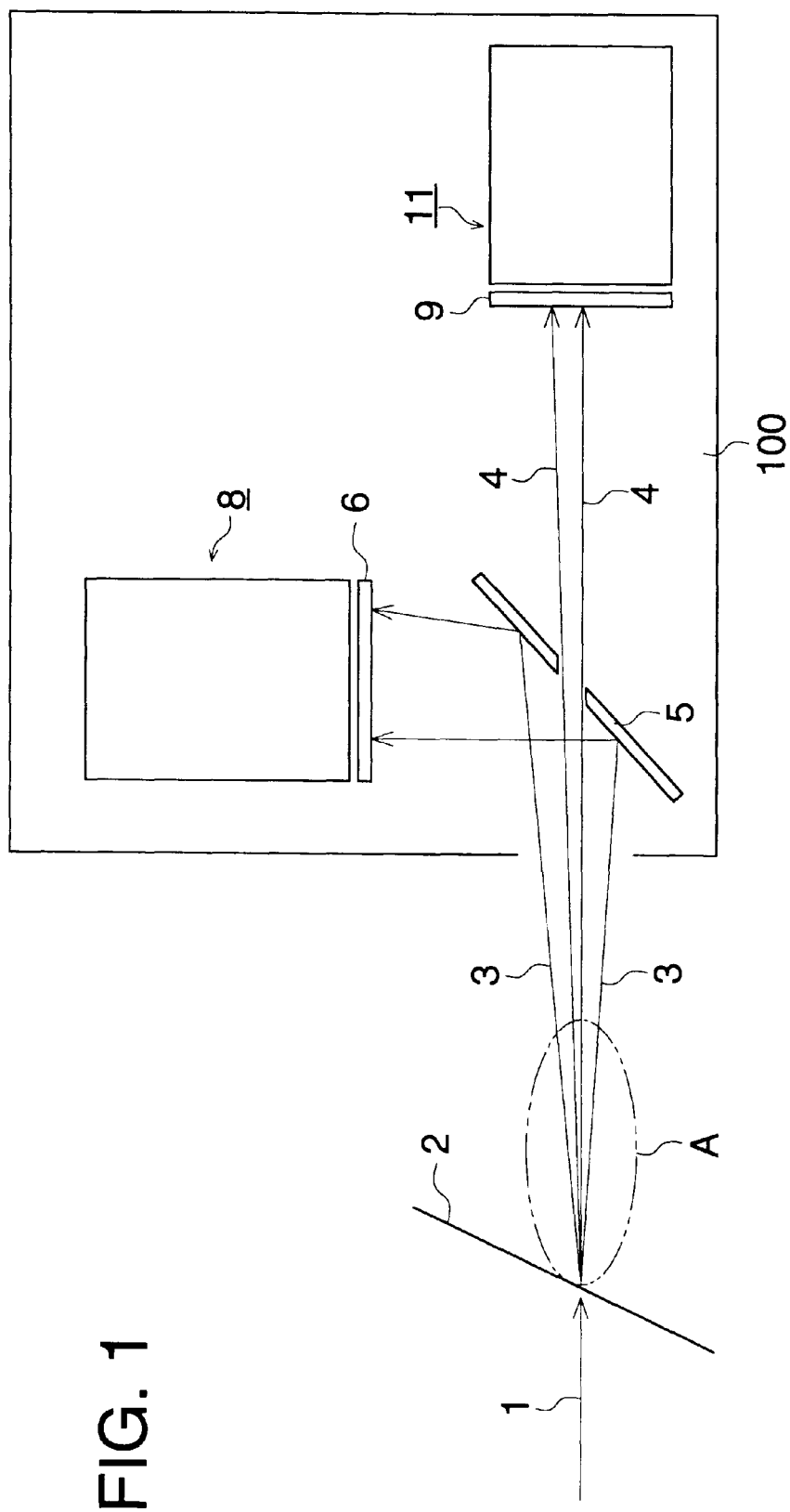
FIG. 1 is an overall general view of the conventional light detecting device in which the regular transmission light and the diffuse transmission light are separated from each other by a slit mirror system, and by which the change of quantity of light of both light is detected.
Figure 2:
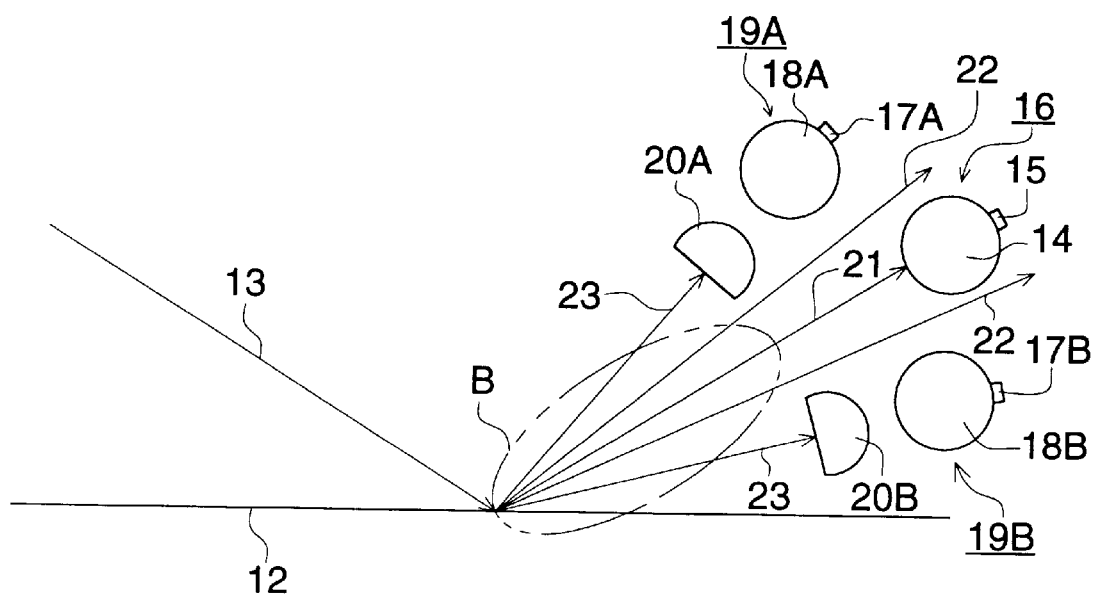
FIG. 2 is an overall general view of the conventional light detecting device in which 3 light guiding members are used and the regular transmission light and the diffuse transmission light are separated from each other, and by which the change of quantity of light of both light is detected.
Figure 3A:
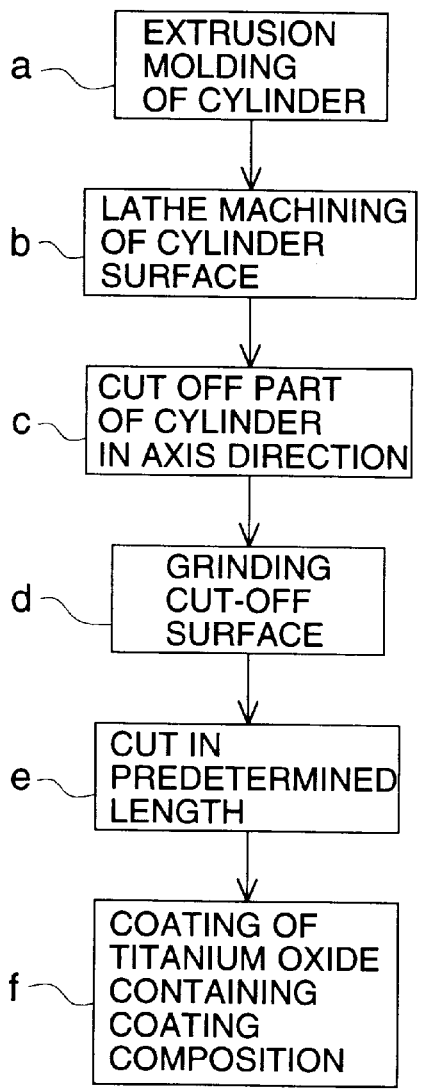
FIGS. 3(*a*) and 3(*b*) are illustrations showing production methods of the light guiding member according to the present invention.
Figure 3B:
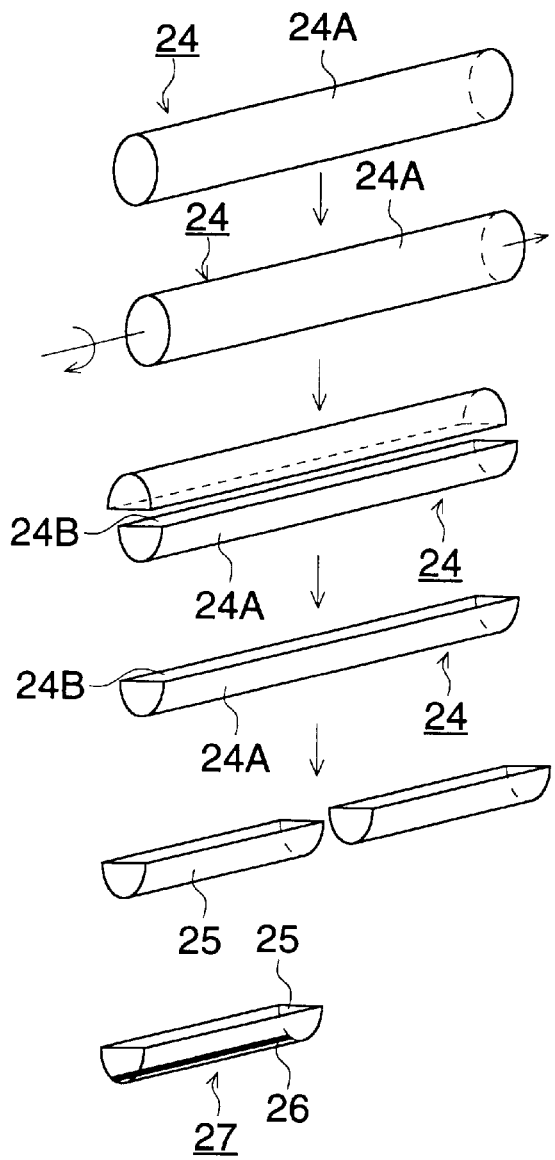

Referring to FIGS. 3(a) and 3(b), a light guiding member of the present invention, and its production method will be described below. FIGS. 3(a) and 3(b) are illustrations showing production processes of the light guiding member according to the present invention.

In the production of the light guiding member 27, initially, resin is extruded and a cylinder 24 having a predetermined length is molded by the extrusion molding (Step a). After molding of the cylinder 24, lathe machining is conducted on the cylinder surface 24A (Step b). After extrusion molding of the cylinder 24, process streaks exist due to a cap or the like. Rotational grinding or buffing is conducted around the axis of the cylinder 24 using a center lathe machine or a lathe, and lathe machining is carried out on the cylinder surface 24A, so that circularity processing can be conducted easily and highly accurately. Next, a portion of the cylinder 24 is cut off such that the cut off surface is parallel to the cylindrical axis (Step c), and the cut off surface 24B is ground by a sand paper or the like (Step d). It is preferable that grinding by the sand paper is conducted in several steps beginning from the rough sand paper to fine sand paper (for example, in the order of #400, #800, #1000, #1200, etc.). This ground surface is defined as the first side surface.

In this connection, the cylinder is preferably formed of transparent acrylic resin because of low cost, easily processed ability, a large refractive index, etc., however, other transparent resin such as transparent plastic, inorganic glass such as quartz glass, etc., may be used.

After grinding the cut off surface 24B, the cylinder is cut into a predetermined length as necessary, and the light transmission member 25 is obtained (Step e). In this connection, cutting processing may not be conducted and extrusion molding may be conducted so that the cylinder is molded into a predetermined length.

A light scattering band 26 is formed in the axial direction with a predetermined width on the curved surface opposite to thus obtained cut off surface 24B of the light transmission member 25 (Step f). Thereby, the light guiding member 27 according to the present invention can be obtained. This curved surface is defined as the second side surface.

The light scattering band 26 is preferably made by coating the coating material containing light scattering particles such as titanium oxide, or the like. More specifically, the light scattering band 26 is preferably formed in such a manner that the coating material made by mixing particles mainly containing titanium oxide with an average particle size of 0.2 $\mu$m–0.3 $\mu$m and cyclohexanone or methyl ethyl ketone, etc., is applicator coated by a blade whose curvature is adjusted to the outer periphery of the light transmission member 25, and thereby the coating material is uniformly coated within the wet film thickness range of 20 $\mu$m–200 $\mu$m and dried. It is also considered that the light scattering band is coated on the cylindrical light transmission member, and then the cylinder is cut. However, as described herein, it is preferable that the light scattering band is coated after cutting the cylindrical light transmission band. Further, when a warp is produced at the time of cutting the cylindrical light transmission member, the light scattering band is preferably coated after correcting the warp. Further, the diameter of cylinder is preferably larger than that of a light guiding member for diffuse reflection light, which will be described later, however, it is not necessarily limited to the above description. Incidentally, a main component of a coating for the light scattering band is not limited to the titanium oxide. A light scattering material such as barium sulfate may be used for the main component.

Figure 9:
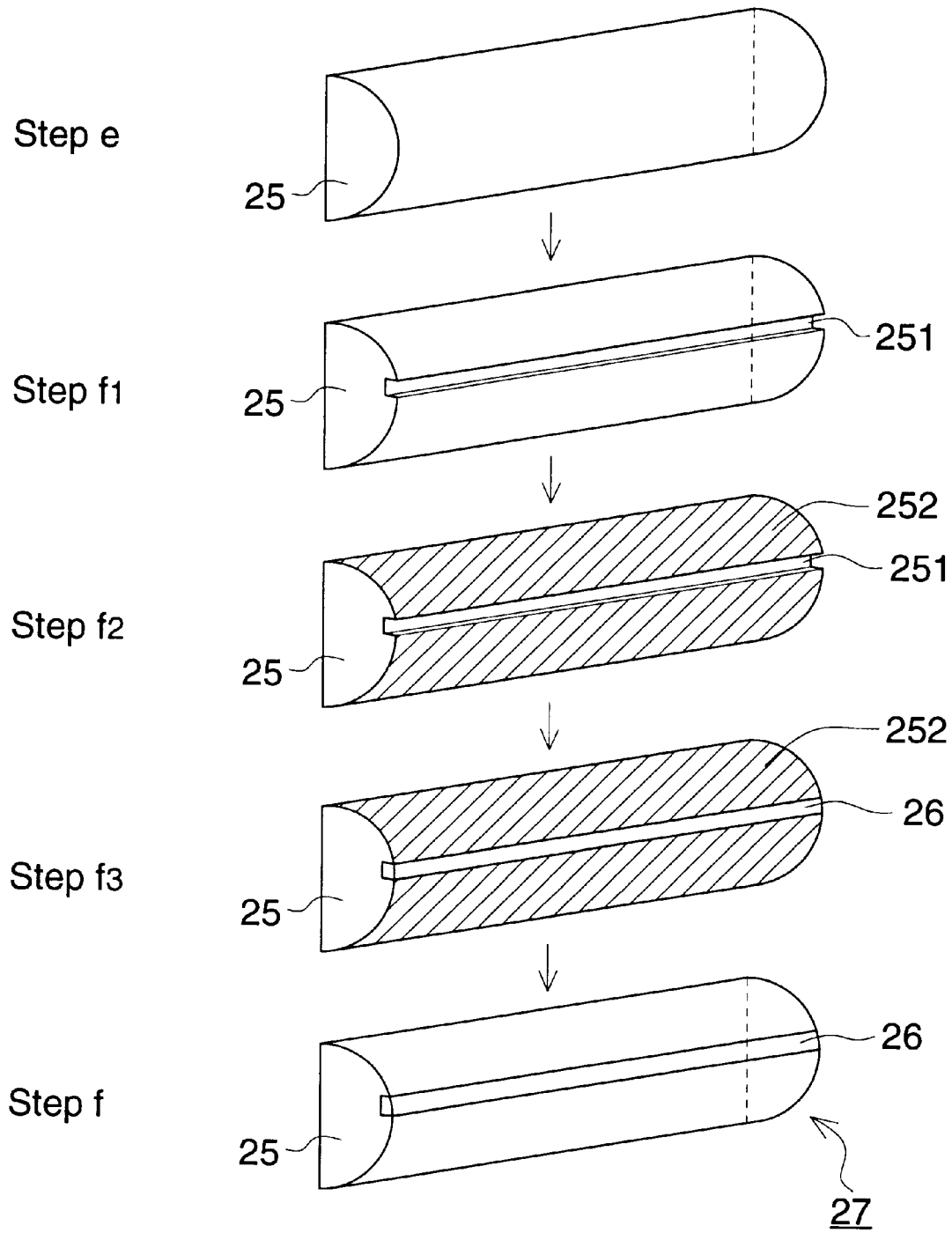
FIG. 9 is an illustration showing an example of a forming method of a light scattering band.
Figure 10:
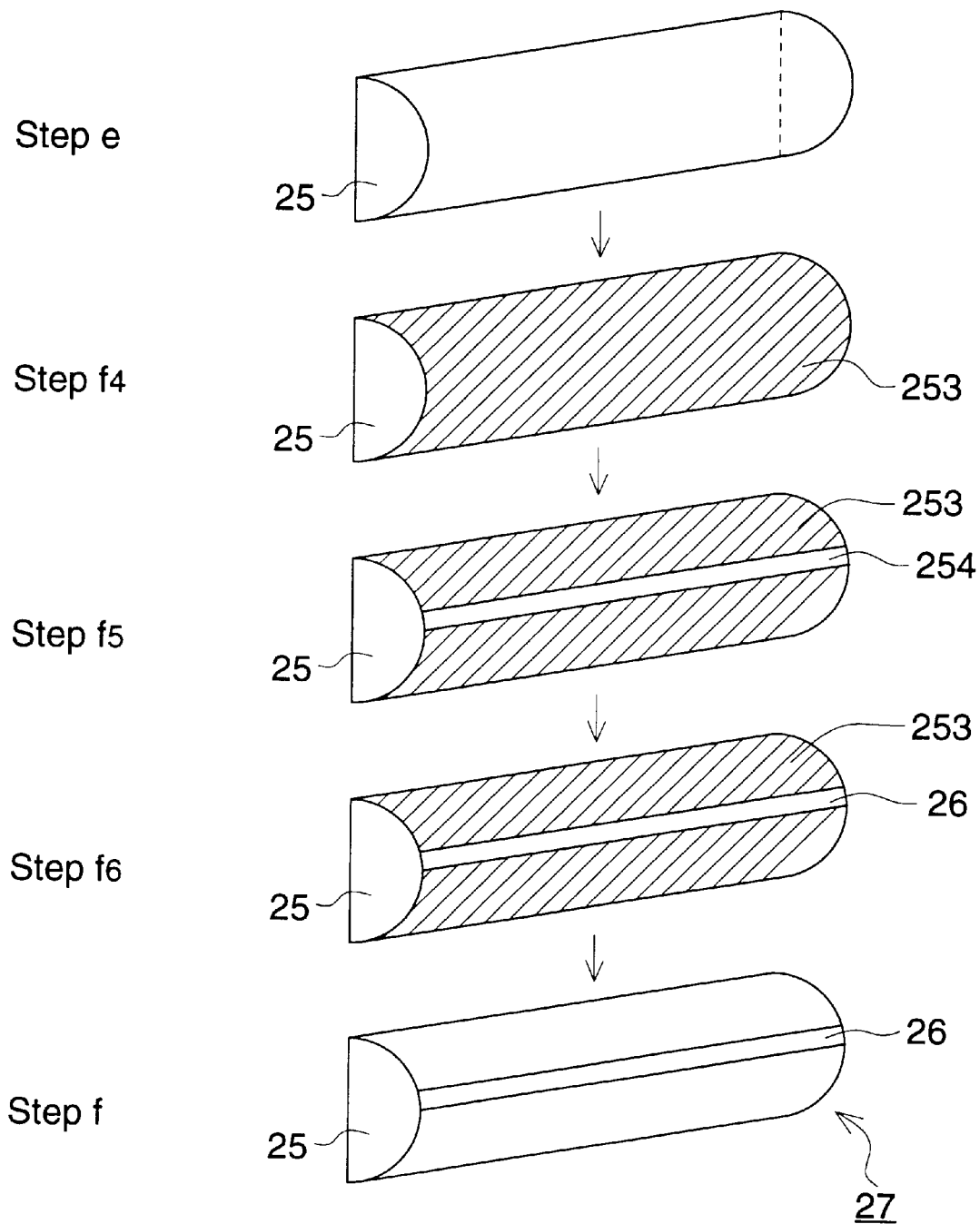
FIG. 10 is an illustration showing an example of a forming method of a light scattering band.

In this connection, the light scattering band 26 is preferably formed by the methods shown in FIG. 9 or FIG. 10 so that the accuracy of the width of the light scattering band is increased when the light scattering band 26 is formed by applicator coating using the blade.

FIG. 9 is a view showing a coating method in which a groove is formed in the direction of cylindrical axis by milling, and the light scattering band is coated in the groove. Milling is conducted on the light transmission member 25 obtained in (Step e) by an end mill, or the like, and a groove 251 with a predetermined width in the direction of cylindrical axis and a predetermined depth, is formed (Step f1). This groove width is the width of the light scattering band. Because the groove 251 is formed by the end mill, or a similar apparatus, the width and the depth of the groove 251 can be highly accurately adjusted. The depth of the groove 251 is preferably 50 $\mu$m–500 $\mu$m.

Next, the side surface of the light transmission member 25 except the groove 251 formed in (Step f1) is covered by a masking tape 252 (Step f2). Even when the masking tape 252 is projected to the groove 251 more or less due to the expansion of the tape 252, the depth of the groove 251 can cover the protruded portion and the high accuracy is maintained. After the masking tape 252 is adhered so that the coating material does not adhere to the side surface except the groove, a light scattering band 26 is applicator coated in the groove 251 by the blade and the light scattering band 26 is formed (Step f3). Finally, the masking tape is peeled off and thus the light guiding member 27 according to the present invention is obtained (Step f).

The light scattering band 26 of the light guiding member 27 made by this method has a sharp edge portion, so that the specular reflection light (regular transmission light) and the diffuse reflection light (diffuse transmission light)can be more highly accurately separated from each other.

Next, FIG. 10 is a view showing a coating method in which a portion of the masking tape previously adhered on the entire side surface of the light transmission member 25 is cut off in a predetermined width in the direction of the cylindrical axis, and the light scattering band is coated on the cut off portion.

The entire side surface of the light transmission member 25 obtained in (Step e) is covered by a masking tape 253 (Step f4). A portion 254 of the masking tape 253 is cut off in a predetermined width in the direction of the cylindrical axis by a tool in which an edge is provided to a height gauge, or a similar tool (Step f5). Then, the light scattering band 26 is formed by applicator coating on the portion 254 in which the masking tape has been cut off, by the blade (Step f6). Finally, the masking tape is peeled off, and thus the light guiding member 27 according to the present invention is obtained (Step f).

The preferable length of the width of the light scattering band 26 changes depending on the size of the light guiding member and the distance from the subject to be inspected to the light guiding member, and it is difficult to regulate the width of the light scattering band 26 by the length. It is preferable to determine the width of the light scattering band 26 so that, in a mounting position of the light guiding member with respect to the subject to be inspected, only the light having the spread angle within a predetermined angle enters the light scattering band 26, in the refection light from the subject to be inspected or transmission light through the subject, and the light having the diverging angle not less than a predetermined angle does not enter the light scattering band 26. The predetermined angle is preferably not more than 5°, and more preferably not more than 3°.

As described above, the light guiding member according to the present invention is produced.

Figure 4:
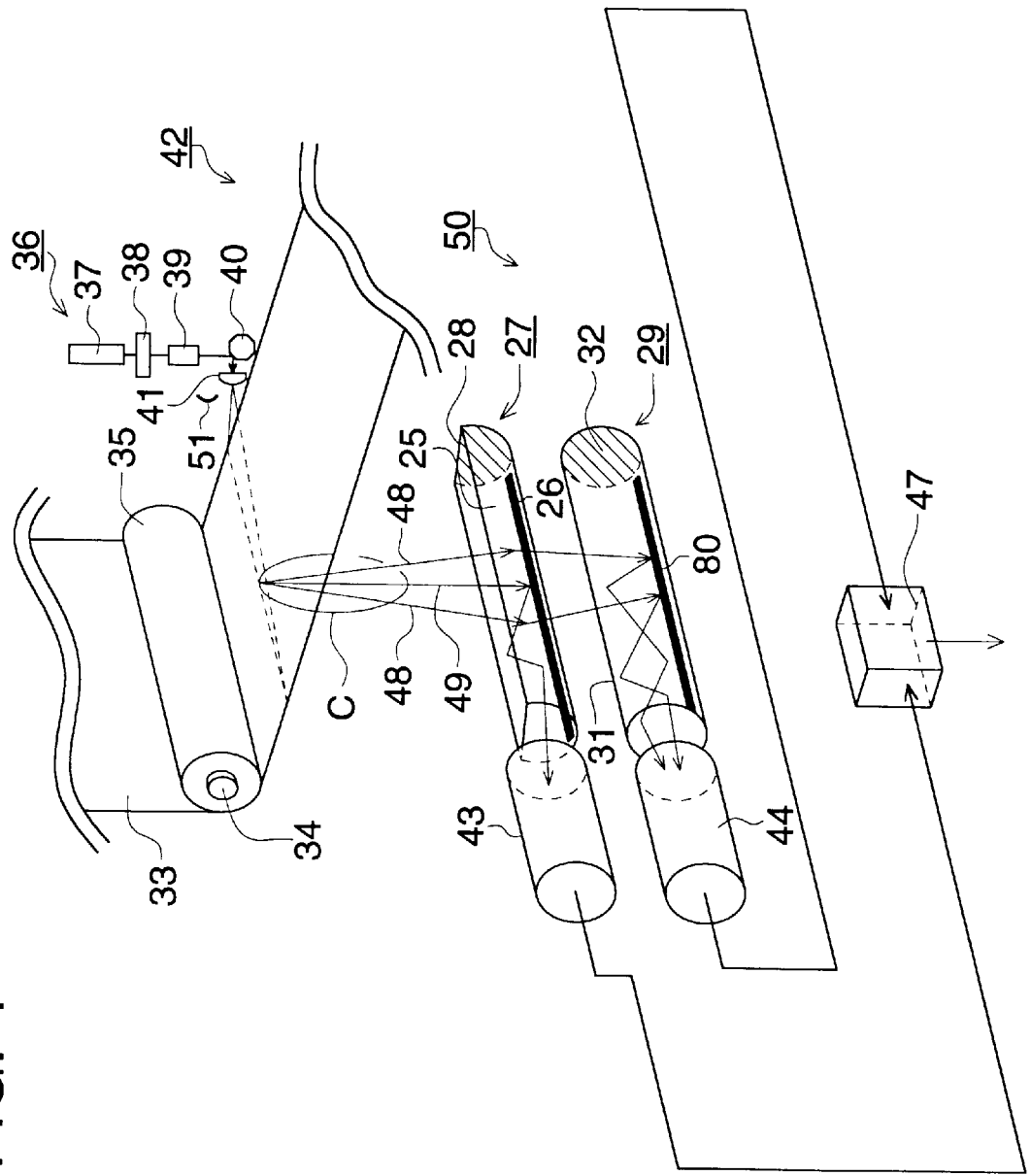
FIG. 4 is an overall general perspective view of a defect inspecting apparatus according to the present invention.

Next, referring to FIG. 4, a light detecting device using the light guiding member according to the present invention, and a defect inspecting apparatus using the light detecting device, will be described below. FIG. 4 is an overall general perspective view of a defect inspecting apparatus according to the present invention.

An object of the defect inspecting apparatus is to detect the coating defect of the subject to be inspected 33 (irradiated object), on which an under coating layer is coated before emulsion is coated on polyethylene terephthalate (PET) film for production of photosensitive photographic film. Of course, the subject to be inspected is not limited to the above object, and the apparatus 42 can also be used for inspection of air-bubble in the laminated film. Of course, the subject may be photosensitive or nonsensitive film.

The defect inspecting apparatus has a conveyance roller 35 to convey the subject to be inspected 33, a flying spot type optical system 36 by which the inspection light, which is a laser light beam, scans on the subject to be inspected 33, and a light detecting device 50 by which the specular reflection light and the diffuse reflection light are separated from each other, and changes of the quantity of both light are detected. The light detecting device 50 has a light guiding member for specular reflection light 27, which is the first light guiding member, by which the specular reflection light 49 is guided to a specular reflection light detecting means 43, in the reflection light which is the irradiated inspection light reflected by the subject to be inspected 33, and the diffuse reflection light 48 is converged and emitted to a guiding member 29 for the diffuse reflection light, which is the second light guiding member; a specular reflection light detecting means 43 to detect a change of quantity of light of the specular reflection light 49 guided by the guiding member 27 for the specular reflection light; the guiding member 29 for the diffuse reflection light to guide the diffuse reflection light 48 to a diffuse reflection light detecting means 44 by which the diffuse reflection light 48 is detected, in the reflection light which is the irradiated inspection light reflected by the subject to be inspected 33; and the diffuse reflection light detecting means 44 to detect the diffuse reflection light 48 guided by the light guiding member for the diffuse reflection light 29.

The subject to be inspected 33 is conveyed through the conveyance roller 35 at a predetermined speed, and the inspection light from the flying spot type optical system 36 scans on the subject to be inspected 33 in the direction of its width.

A rotary encoder 34 is provided on the conveyance roller 35 and outputs conveyance pulses. By counting the conveyance pulses, the conveyance speed of the subject to be inspected is detected, and the conveyance speed may be adjusted by feeding back it to the conveyance roller 35.

The flying spot type optical system 36 is composed of a laser beam source 37, an ND filter 38, a condenser lens group 39, a polygonal mirror 40, an F θ lens 41, and a shutter 51, and emits the inspection light onto the subject to be inspected, and scans on it as described below. As the laser beam source 37, for example, He—Ne laser, or the like, can be used. Further, when the subject to be inspected is a photosensitive material, it is necessary to use the light source having a wavelength and intensity by which the subject to be inspected is not fogged.

The inspection light from the laser beam source 37 is dimmed out by the ND filter, reflected by the rotating polygonal mirror 40, and scans on the surface of the subject to be inspected 33 in the direction of its width through the F θ lens 41. When no scanning is conducted, the light beam is shut off by the shutter 51.

The inspection light scanning in the direction of the width of the subject to be inspected by the flying spot type optical system 36, is reflected on the subject to be inspected 33, becomes the specular reflection light and the diffuse reflection light, and changes of the quantity of each reflection light are detected by the light detecting device 50. The light detecting device 50 will be described below. The light guiding member for the specular reflection light 27 and the light guiding member for the diffuse reflection light 29 of the light detecting device 50 are located opposite to the subject to be inspected 33.

The light guiding member for the specular reflection light 27, which is the first light guiding member, is disposed in a position in which the reflection light of the inspection light scanning in the direction of width of the subject to be inspected 33 by the flying spot type optical system 36, can be received, almost in parallel with the subject to be inspected, and the direction of its axis is in parallel with the scanning direction of the scanning light. Further, the light guiding member for the diffuse reflection light 29, which is the second light guiding member, is disposed almost in parallel with the light guiding member for the specular reflection light 27 and on the optical axis of the specular reflection light, and beyond the light guiding member for the specular reflection light viewed from the subject to be inspected 33.

The light guiding member for the specular reflection light 27 is the light guiding member 27, whose production method is described in FIG. 3, in which the light scattering band 26, which is the first light scattering band, is coated in the axial direction on the curved surface of the light transmission member, which is the first cylindrical light transmission member, in which a part of the cylinder is cut off in the axial direction. The light guiding member for the specular reflection light 27 is disposed such that the first side surface, which is a flat surface portion of the light guiding member 27, is a light receiving surface and faces the direction in which the reflection light comes, and the light scattering band 26 provided on the second side surface is on the optical axis of the specular reflection light. The width of the light scattering band 26 is determined so that it receives only the reflection light whose diverging angle is within 5°, in the mounting position of the light guiding member for the specular reflection light 27. A mirror surface 28 is provided on one circular end surface of the light guiding member for the specular reflection light 27, so that it faces toward the inside of the light guiding member for the specular reflection light 27, and the light entered the inside of the light guiding member for the specular reflection light 27 does not go out from the circular end surface. Further, the width of the light scattering band 26 is preferably determined so that only the reflection light, whose diverging angle is within 3° in the mounting position of the light guiding member for the specular reflection light 27, is received.

In this connection, in the light guiding member for the specular reflection light 27, the fist side surface is preferably the plane, however, the curved surface may also be acceptable. Further, as the light guiding member for the diffuse reflection light 29, a member is used in which the light scattering band 80, which is the second light scattering band, is provided in a predetermined width by coating a coating material mainly containing titanium oxide particles on the cylindrical light transmission member 31, which is the second cylindrical light transmission member. The same material as that of the light guiding member for the specular reflection member 27 can be used as the material of the cylindrical light transmission member 31, and the same material as that of the light scattering band of the light guiding member for the specular reflection light 27 can be used as the material of the light scattering band 80 of the light transmission member 31. Further, a mirror surface 32 is provided on one circular end surface of the light guiding member for the diffuse reflection light 29, so that it faces toward the inside of the light guiding member for the diffuse reflection light 29, and the light entered the inside of the light guiding member for the diffuse reflection light 29 does not go out from the circular end surface.

Figure 11:
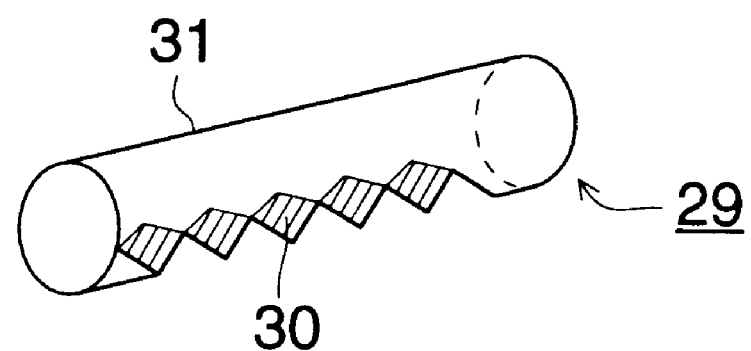
FIG. 11 is a perspective view showing an example of the light guiding member for diffuse reflection light.

In this connection, as the light guiding member for the diffuse reflection light 29, as shown in FIG. 11, a member is also acceptable in which a plurality of V-shape grooves are provided in almost perpendicular to the direction of the cylindrical axis in the cylindrical light transmission member 31, formed of transparent acrylic resin, and a mirror 30 is provided on the surface of the V-shape groove as the light reflection surface, facing toward the inside of the light guiding member for diffuse reflection light 29. In this connection, when the deepest part of the plurality of V-shape grooves is viewed from the direction of the cylindrical axis, it is almost linear. That is, each depth of the plurality of V-shape grooves is uniform.

Figure 5:
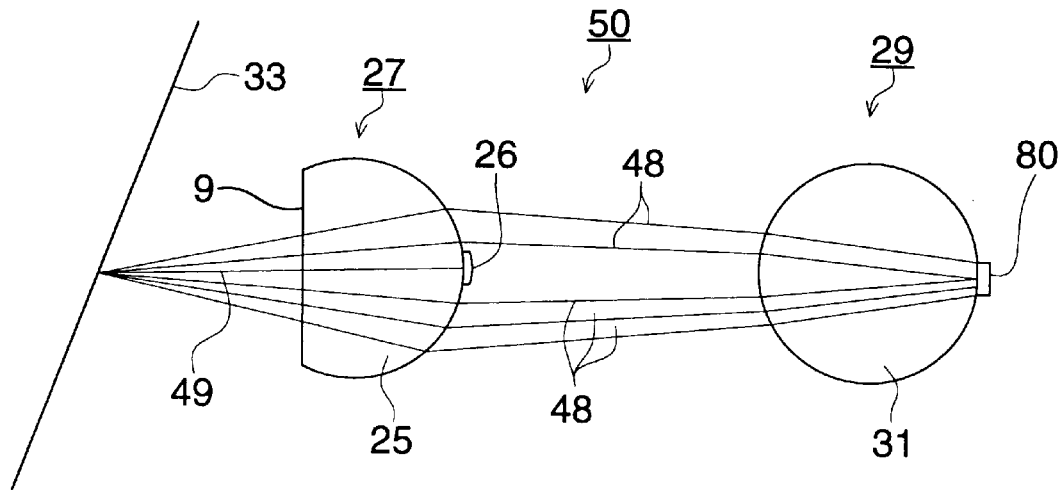
FIG. 5 is an illustration to explain a light separation system of the specular reflection light and the diffuse reflection light by the light guiding member and the light detecting means of the present invention, by using a side sectional view of the light guiding member for specular reflection light and the light guiding member for diffuse reflection light in the light detecting device according to the present invention.

Here, referring to FIG. 5, how the 2 kinds of reflection lights, that is, the specular reflection light and the diffuse reflection light are separated from each other by the light guiding member according to the present invention, will be described below. FIG. 5 is an illustration to explain the mechanism of the light separation of the specular reflection light and the diffuse reflection light by the light guiding member and the light detection means of the present invention, by using a side sectional view of the light guiding member for the specular reflection light 27 and the light guiding member for the diffuse reflection light 29 of the light detecting device 50.

The inspection light (not shown) emitted from the flying spot type optical system 36 scans the subject to be inspected 33 in the direction of its width, is reflected by the subject to be inspected 33, and becomes the specular reflection light 49 and the diffuse reflection light 48. Both the specular reflection light 49 and the diffuse reflection light 48 enter from the plane (the first side surface 9), which is the light receiving surface of the light guiding member for the specular reflection light 27, into the light guiding member for the specular reflection light 27.

The specular reflection light 49 entered into the light guiding member for the specular reflection light 27 is scattered by the light scattering band 26 formed on the second side surface, which is the curved surface opposite to the first side surface, and the scattered specular reflection light 49 is guided to the circular end surface in the direction of the cylindrical axis (in the direction perpendicular to the drawing) in the light guiding member for the specular reflection light 27 (not shown in the drawing). The width of the light scattering band 26 is determined depending on the range of the diverging angle of the light separated at the mounting position of the light guiding member for the specular reflection light 27, and in the present example, the width of the light scattering band 26 is determined so that the reflection light, whose diverging angle is not larger than 5°, is received by the light scattering band 26. The narrower is the width of the light scattering band, the higher the separation efficiency of the specular reflection light 49 and the diffuse reflection light 48 increases. However, severer positioning is necessary for the light guiding member for the specular reflection light 27.

On the other hand, the diffuse reflection light 48 entered the light guiding member for the specular reflection light 27 is converged by the lens effect by the second side surface, which is the curved surface, opposite to the first side surface, which is the light receiving surface, of the light guiding member for the specular reflection light 27, and emitted from the second side surface toward the light guiding member for the diffuse reflection light 29. The diffuse reflection light 48, converged by the second side surface of the light guiding member for the specular reflection light 27 and emitted from that, enters from the side surface of the cylinder of the light guiding member for the diffuse reflection light 29 into the light guiding member for the diffuse reflection light 29, scattered by the light scattering band 80 provided on the curved surface opposite to the incident surface, and the scattered diffuse reflection light 48 is guided to the end surface in the direction of the cylindrical axis (in the direction perpendicular to the paper) in the light guiding member for the diffuse reflection light 29 (not shown in the drawing).

Accordingly, one dimensional or two dimensional reflection light is guided to one point by the light guiding member for the specular reflection light 27 and light guiding member for the diffuse reflection light 29.

As described above, in the present example, the specular reflection light 49 and the diffuse reflection light 48 (the light having the diverging angle not less than 5°) are separated from each other by the light guiding member 27 according to the present invention, the specular reflection light 49 is guided in the direction of the cylindrical axis of the light guiding member for the specular reflection light 27, and the diffuse reflection light 48 is guided in the direction of the cylindrical axis of the light guiding member for the diffuse reflection light 29.

Accordingly, the diffused light near the specular reflection light 49, which has useful information for the defect inspection, and the specular reflection light 49 can easily be separated from each other by the light guiding member according to the present invention, when the width of the light scattering band 26 of the light guiding member for the specular reflection light 27 is narrowed. Further, the diffused light can be converged and emitted by the lens effect of the second side surface of the light guiding member according to the present invention, the loss of the diffused light in the advancing process from the light guiding member for the specular reflection light 27 to the light guiding member for the diffuse reflection light 29 can be reduced, and much more diffused light can be received in the light guiding member for the diffuse reflection light 29. The loss of the quantity of light due to reflection of the received light on the light receiving surface can be more reduced than that of the curved surface of the cylindrical light guiding member because the curvature of the first side surface, which is the light receiving surface, of the light guiding member according to the present invention is 0, which is the plane, and a large quantity of received light can be entered the inside of the light guiding member. Further, both of the light separation and the light convergence are conducted by only one light guiding member according to the present invention, and thereby, the loss of the quantity of the specular reflection light and the diffuse reflection light can be more reduced than that of the case in which a plurality of members are used, and the device can be made simple.

In FIG. 4, the specular reflection light 49 guided in the direction of the cylindrical axis of the light guiding member for the specular reflection light 27, is emitted from one circular end surface on which the mirror 28 of the light guiding member for the specular reflection light 27 is not provided. A specular reflection light detecting means 43, which is the first light detecting means, is provided on the circular end portion of the light guiding member for the specular reflection light 27 such that the light receiving surface is opposed to the circular end surface of the light guiding member for the specular reflection light 27. The specular reflection light emitted from the one circular end surface of the light guiding member for the specular reflection light 27 is detected by the specular reflection light detecting means 43. The specular reflection light detecting means 43 is composed of, for example, a photo-electric converter such as a PMT, a photodiode or the like, and the detected specular reflection light is converted into an electric signal and a predetermined output wave-form is obtained. When defects such as the existence or non-existence of the coating layer, change of the layer thickness, etc., are generated on the subject to be inspected, deformed portions such as convex portions or concave portions are generated on the output wave-form, and the defect can be detected from the wave-form.

On the other hand, the diffuse reflection light 48 guided in the direction of the cylindrical axis of the light guiding member for the diffuse reflection light 29, is emitted from one circular end surface on which the mirror 32 of the light guiding member for the diffuse reflection light 29 is not provided. The diffuse reflection light detecting means 44, which is the second light detecting means, is provided on the circular end portion of the light guiding member for the diffuse reflection light 27 such that the light receiving surface is opposed to the circular end surface of the light guiding member for the diffuse reflection light 29, and the diffuse reflection light emitted from the one circular end surface of the light guiding member for the diffuse reflection light 29 is detected by the reflection light detecting means 44. The diffuse reflection light detecting means 44 is composed of, for example, the photo-electric converter such as the PMT, or the like, and the detected diffuse reflection light is converted into an electric signal and a predetermined output wave-form is obtained. When defects such as the existence or non-existence of the coating layer, change of the layer thickness, etc., are generated on the subject to be inspected, deformed portions such as convex portions or concave portions are generated on the output wave-form, and the defect can be detected from the wave-form.

The output obtained by the specular reflection light detecting means 43 and that obtained by the diffuse reflection light detecting means 44 are sent to a comparator 47. In the comparator 47, the change of quantity of light of the specular reflection light and that of the diffuse reflection light are compared, and thereby the difference between the distributions of quantity of reflection light of the specular reflection light and the diffuse reflection light can be obtained. Thereby, not only the existence or non-existence of the defect on the subject to be inspected 33, but also types of defects such as the hole-shape defect, mixture of foam or foreign matters, change of layer thickness, or the like, can be distinguished to some extent from the difference between distributions of quantity of reflection light of the specular reflection light and diffuse reflection light, and therefore, the more accurate defect inspection can be conducted. More specifically, foam, dust or foreign matters, or the like, mixed at the time of lamination, can be accurately detected, and the type of the defect can also be discriminated.

Figure 6:
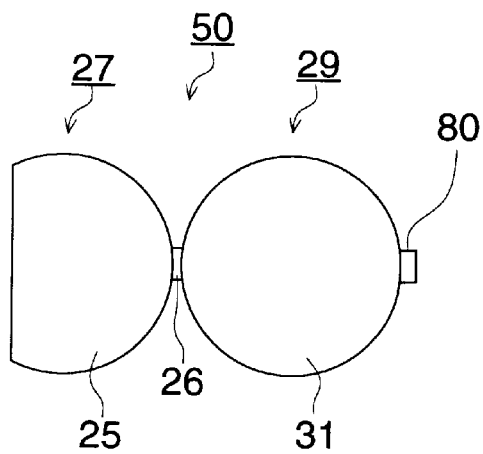
FIG. 6 is a side sectional view of a part of another example of the light detecting device according to the present invention.

Referring to FIG. 6, another example of the light detecting device according to the present invention will be described below. FIG. 6 is a side sectional view of a part of another example of the light detecting device according to the present invention.

This light detecting device 50 is characterized in that the light guiding member for the specular reflection light 27 and the light guiding member for the diffuse reflection light 29 are located in contact with each other. Other structure of the light detecting device 50 is the same as that of the light detecting device 50 described in FIG. 4. Further, the light guiding member for the specular reflection light 27 and the light guiding member for the diffuse reflection light 29 are also the same as those in the preceding example. This type of light detecting device 50 may also be acceptable.

Figure 7:
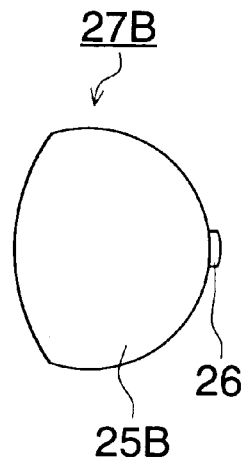
FIG. 7 is a side sectional view of another example of the light guiding member according to the present invention.
Figure 8:
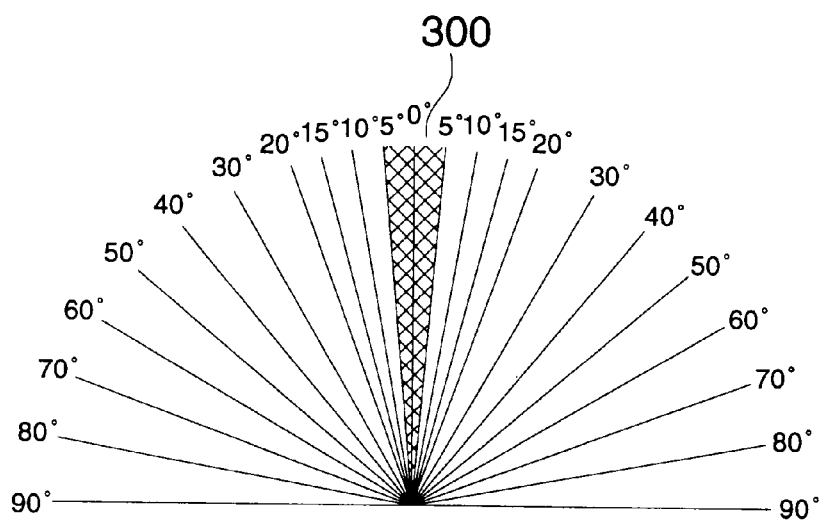
FIG. 8 is an illustration to explain a diverging angle.

Referring to FIG. 7, another example of the light guiding member according to the present invention will be described. FIG. 7 is a side sectional view of another example of the light guiding member according to the present invention.

A light guiding member 27B in FIG. 7 is formed as follows. The coating material mainly containing titanium oxide particles is coated on a light transmission member 25B having the shape in which a part of the cylindrical light transmission member formed of transparent acrylic resin is cut off, so that the light scattering band 26 is provided in the direction of cylindrical axis with a predetermined width, and its first side surface is not flat, but curved surface. The curvature of the first side surface is smaller than that of the opposed curved surface. When the first side surface is used as the light receiving surface, the light converging efficiency of the diffused light into the light guiding member is increased, therefore, this light guiding member 27B is preferable.

When the photosensitive material such as photographic light sensitive material is used as the subject to be inspected, generally, the very small quantity of inspection light is used so as to prevent fogging. In the light guiding member, light detecting device and defect inspecting apparatus of the present example according to the present invention, the loss of the reflection light, specifically, the diffuse reflection light is small, and the very much small quantity of diffuse reflection light of the small quantity of light can be effectively guided, thereby the more accurate defect inspection can be performed. Accordingly, the light guiding member, light detecting device and defect inspecting apparatus of the present example according to the present invention are more effective when the photosensitive material such as the photographic light sensitive material is used as the subject to be inspected.

Of course, the light guiding member, light detecting device and defect inspecting apparatus of the present example according to the present invention can be used not only for the reflection light, but also for the case where transmission light is detected in which the inspection light transmits the subject to be inspected. In this connection, it may also be allowed that the light detecting device is provided such that the light guiding member for the diffuse reflection light, which is the second light guiding member, is not provided, and the light emitted from the second side surface is directly detected.

According to the present invention, the regular transmission light (or the specular reflection light) and the diffuse transmission light (or the diffuse reflection light) can be separated from each other, and the size of the light detecting device to detect the change of the quantity of light of both light can be reduced, the device can be made so simple, and its cost can be lowered.

Further, according to the present invention, the loss of the diffuse transmission light (or the diffuse reflection light) is reduced, thereby, the more diffuse transmission light (or the diffuse reflection light) can be received and detected, and the loss of the diffuse transmission light (or the diffuse reflection light) can be reduced. Thereby, even when the quantity of light is very small at the time of the defect inspection for the photographic light sensitive material, the defect inspection for the photographic light sensitive material by the light detection can be accurately conducted.

Still further, according to the present invention, the diffuse transmission light (or the diffuse reflection light) having small diffusiveness, and the diffuse transmission light (or the diffuse reflection light) near the regular transmission light (or the specular reflection light) can be obtained, thereby, the light detection and defect inspection can be easily and more accurately conducted.

What is claimed is:

1. A defect inspecting apparatus for optically inspecting a defect of a subject to be inspected, comprising:
    (a) a first light guiding member comprising
        a first columnar light transmitting member including a first side surface and a second side surface facing the first side surface, curvature of the first side surface being smaller than that of the second side surface, and
        a first light scattering band having a definite width provided on the second side surface of the first columnar light transmitting member in a columnar axis direction,
        wherein the first light guiding member enables a transmitted light or a reflected light of a light illuminated to the subject to be inspected from a light source to enter the first side surface, a part of the light incident on the first side surface to guide substantially to the columnar axis direction of the first light guiding member thereby to reach an end thereof, the other part of the light incident on the first side surface to emit from the second side surface;
    (b) a first light detecting means for detecting the light guided to the circular end of the first light guiding member; and
    (c) a light detecting device for detecting the light emitted from the second side surface of the first light guiding member.

2. The defect inspecting apparatus of claim 1, wherein the light detecting device comprises:
    a second light guiding member comprising
        a second columnar light transmitting member, and
        a second light scattering band having a definite width provided on a side surface of the second columnar light transmitting member in a columnar axis direction,
        wherein the second light guiding member enables the light emitted from the second side surface of the first light guiding member to enter the second columnar light transmitting member, and the light incident to guide substantially to a columnar axis direction of the second light guiding member thereby to reach an end of the second light guiding member; and
    a second light detecting device for detecting a light guided to an end of the second light guiding member.

3. The defect inspecting apparatus of claim 1, wherein curvature of the first side surface of the first light guiding member is smaller than that of a circumference of a circle having the same area as a section perpendicular to the columnar axis direction of the first columnar light transmitting member.

4. The defect inspecting apparatus of claim 1, wherein the first side surface of the first light guiding member is plane.

5. The defect inspecting apparatus of claim 1, wherein the first columnar light transmitting member is formed in such a manner that a part of a cylindrical light transmitting member is cut off so that the part cut off is plane and substantially parallel to the columnar axis of the first columnar light transmitting member.

6. The defect inspecting apparatus of claim 1, wherein one circular end of the first columnar light transmitting member is formed by a specular surface.

7. The defect inspecting apparatus of claim 1, wherein the first light guiding member substantially guides a regular transmission light of the light illuminated to the subject to be inspected from the light source in the columnar axis direction of the first light guiding member, and substantially emits a diffuse transmission light of the light illuminated to the subject to be inspected from the light source from the second side surface.

8. The defect inspecting apparatus of claim 1, wherein the first light guiding member substantially guides a specular reflection light of the light illuminated to the subject to be inspected from the light source in the columnar axis direction of the first light guiding member, and substantially emits a diffuse reflection light of the light illuminated to the subject to be inspected from the light source from the second side surface.

9. The defect inspecting apparatus of claim 1 further comprising an optical system for emitting a light scanning a surface of the subject to be inspected in a predetermined direction.

10. The defect inspecting apparatus of claim 1, wherein the first light guiding member guides a light having a diverging angle of not more than a predetermined angle among the incident light in the columnar axis direction of the first light guiding member, and emits a light having a diverging angle of more than the predetermined angle among the incident light from the second side surface, and wherein the predetermined angle is not more than 5°.

11. The defect inspecting apparatus of claim 2, wherein the second columnar light transmitting member is a cylindrical light transmitting member.

12. The defect inspecting apparatus of claim 1, wherein the first light scattering band comprises a coating containing a light scattering material.

13. The defect inspecting apparatus of claim 2, wherein the second light scattering band comprises a coating containing a light scattering material.

14. The defect inspecting apparatus of claim 2, wherein the second light scattering band comprises:
    a groove-shaped band in which a plurality of grooves are formed perpendicular to or at a predetermined angle with respect to the columnar axis direction of the second columnar light transmitting member, continuously with a predetermined distance therebetween, in parallel to each other, each sectional shape of the grooves is formed by a triangle or a curved surface, and each deepest portion of the grooves is substantially aligned in a straight line when viewed from the columnar axis direction; and a specular portion in closely contact with the groove-shaped band.

* * * * *